(12) United States Patent
Seiberg

(10) Patent No.: US 10,675,233 B2
(45) Date of Patent: Jun. 9, 2020

(54) COMPOSITIONS CONTAINING NATURAL EXTRACTS AND USE THEREOF FOR SKIN AND HAIR

(71) Applicant: Seiberg Consulting, LLC, Princeton, NJ (US)

(72) Inventor: Miri Seiberg, Princeton, NJ (US)

(73) Assignee: Seiberg Consulting, LLC, Princeton, NJ (US)

( * ) Notice: Subject to any disclaimer, the term of this patent is extended or adjusted under 35 U.S.C. 154(b) by 158 days.

(21) Appl. No.: 15/342,947

(22) Filed: Nov. 3, 2016

(65) Prior Publication Data

US 2017/0135925 A1    May 18, 2017

Related U.S. Application Data

(60) Provisional application No. 62/256,803, filed on Nov. 18, 2015.

(51) Int. Cl.

| A61K 8/44 | (2006.01) |
|---|---|
| A61Q 5/10 | (2006.01) |
| A61Q 19/04 | (2006.01) |
| A61K 36/04 | (2006.01) |
| A61K 36/28 | (2006.01) |
| A61K 36/48 | (2006.01) |
| A61K 8/9706 | (2017.01) |
| A61K 8/97 | (2017.01) |
| A61Q 19/02 | (2006.01) |
| A61K 8/06 | (2006.01) |
| A61K 8/34 | (2006.01) |
| A61K 8/41 | (2006.01) |
| A61K 8/46 | (2006.01) |
| A61K 8/60 | (2006.01) |
| A61K 8/67 | (2006.01) |
| A61K 8/73 | (2006.01) |
| A61K 8/81 | (2006.01) |
| A61K 8/88 | (2006.01) |
| A61K 8/891 | (2006.01) |
| A61K 8/92 | (2006.01) |
| A61Q 5/00 | (2006.01) |

(52) U.S. Cl.
CPC ............. *A61K 8/447* (2013.01); *A61K 8/062* (2013.01); *A61K 8/34* (2013.01); *A61K 8/345* (2013.01); *A61K 8/347* (2013.01); *A61K 8/41* (2013.01); *A61K 8/46* (2013.01); *A61K 8/60* (2013.01); *A61K 8/676* (2013.01); *A61K 8/732* (2013.01); *A61K 8/8147* (2013.01); *A61K 8/88* (2013.01); *A61K 8/891* (2013.01); *A61K 8/922* (2013.01); *A61K 8/97* (2013.01); *A61K 8/9706* (2017.08); *A61K 36/04* (2013.01); *A61K 36/28* (2013.01); *A61K 36/48* (2013.01); *A61Q 5/00* (2013.01); *A61Q 5/10* (2013.01); *A61Q 19/02* (2013.01); *A61Q 19/04* (2013.01); *A61K 2800/48* (2013.01); *A61K 2800/51* (2013.01); *A61K 2800/522* (2013.01); *A61K 2800/524* (2013.01); *A61K 2800/594* (2013.01); *A61K 2800/5922* (2013.01); *A61K 2800/782* (2013.01)

(58) Field of Classification Search
None
See application file for complete search history.

(56) References Cited

U.S. PATENT DOCUMENTS

| 2005/0065206 A1 | 3/2005 | Kato et al. |
|---|---|---|
| 2007/0166266 A1 | 7/2007 | Dillon et al. |
| 2010/0098732 A1* | 4/2010 | Tippens ................... A61K 8/64 424/401 |
| 2011/0038882 A1* | 2/2011 | Chiang .................. A61K 31/40 424/184.1 |

FOREIGN PATENT DOCUMENTS

| CN | 104940049 | 9/2015 |
|---|---|---|
| FR | 2867973 | 9/2005 |
| JP | 0812552 | 1/1996 |
| JP | 2000/319120 | 11/2000 |
| JP | 2002/205950 | 7/2002 |
| JP | 2008137923 | 6/2008 |
| WO | WO 2004/071519 | 8/2004 |
| WO | WO2007/084769 | 7/2007 |
| WO | WO 2009/067095 | 5/2009 |

OTHER PUBLICATIONS

Diaz Bayona et al., Activity of Sulfated Polysaccharides from Microalgae Porphyridium cruentum over Degenerative Mechanisms of the skin, 2012, International J Science and Advanced Technology, 2: 85-92.*
Mei Jing Piao et al., "Protective Effect of the Ethyl Acetate Fraction of Sargassum muticum Against Ultraviolet B-Irradiated Damage in Human Keratinocytes," Int. J. Mol. Sci. Nov. 2011, 12:8146-8160.
De Jesus Raposo et al., "Bioactivity and Applications of Sulphated Polysaccharides from Marine Microalgae," Mar. Drugs 2013; 11(1):233-252.

(Continued)

*Primary Examiner* — Terry A McKelvey
*Assistant Examiner* — Catheryne Chen
(74) *Attorney, Agent, or Firm* — Fish & Richardson P.C.

(57) ABSTRACT

The present disclosure relates to compositions containing a natural extract(s) and their fraction(s) and the use of such compositions for treatment of skin, hair and nail. For example, the present disclosure relates to compositions containing an aqueous extract of (i) Yacon leave, (ii) Amor Seco leave, or (iii) *Porphyridium* biomass, or a combination thereof and a pharmaceutically or cosmetically acceptable carrier use on hair skin and nails for cosmetic purposes.

7 Claims, No Drawings

(56) References Cited

OTHER PUBLICATIONS

Ishikawa et al., "Anti-Melanogenic Activity of Yacon Leaves in Mouse Melanoma Cells," Animal Cell Technology: Basic & Applied Aspects, 2010; 16:359-364.
Rajasulochana et al., "Glimpses on cosmetic applications using marine red algae," IJPT Sep. 2015; 7(2):9235-9242.
International Search Report and Written Opinion in corresponding PCT Application No. PCT/US 16/60306, dated Jun. 6, 2017, pp. 1-13.
Extended European Search Report in corresponding Application No. 16866845.7, dated Jul. 8, 2019, pp. 1-11.
Rejane B. Oliveira et al., "Topical anti-inflammatory activity of yacon leaf extracts," Revista Brasileria de Farmacognosia-Brazilian Journal of Pharmacognosy: 23(3):497-505 (2013).
N.N: "Amor Seco," Wikipedia Jun. 26, 2019.

\* cited by examiner

COMPOSITIONS CONTAINING NATURAL EXTRACTS AND USE THEREOF FOR SKIN AND HAIR

RELATED APPLICATIONS

This application claims priority to U.S. Application Ser. No. 62/256,803, filed Nov. 18, 2015, the entire contents of which is hereby incorporated by reference.

BACKGROUND

Hair graying (canities), or the loss of pigment production and deposition within the hair shafts, is an obvious sign of aging, which is highly undesirable in many cultures. Hair graying is a complex phenomenon resulting from the interaction of several intrinsic and extrinsic factors. Intrinsic factors may include genetically programmed processes that could lead to premature graying, genetic diseases, and intrinsic aging processes. Extrinsic factors may include environmental factors (e.g. wind, heat, cigarette smoke, chemicals, UV irradiation, etc.), nutritional effects, medications effects, and emotional stress. All these elements induce molecular and cellular processes that contribute to the loss of hair pigmentation.

The major approach to address hair graying is hair dyeing ("coloring"), which was documented archeologically from about 1500 BC, and is still popular today. However, hair coloring has several limitations. The borderline of the hair coloring area becomes visible as hairs grow, creating a less aesthetic appearance than desired, and disclosing the undesired aging process. Hair dyeing requires the use of chemicals that are unhealthy or destructive to the hair or the surrounding skin, as well as to the environment, such as hydrogen peroxide. Professional hair dyeing is associated with significant costs and schedule obligations, and home procedures entail a major time commitment, staining and disorder. It is desired, therefore, to have better procedures and methods to solve the hair graying problem.

It is desired to have a topical treatment that could prevent, slow, reduce or reverse hair graying. It is more desired to have such a treatment as a single and affordable topical treatment for daily skin and hair care. Such a treatment should provide solutions to hair graying with little or no irritation and few or no negative side effects and should further provide other desired scalp and hair health, wellness and beautifying benefits. It is further desired to have a topical treatment that does not require a pharmaceutical prescription.

Skin aging is a slow, chronic process, in which the functionality of skin molecules and structures is reduced with time and is further compromised with UV exposure. Skin aging is first noticed with the appearance of facial sagging, fine lines, wrinkles and age spots, followed by the appearance of dull and thinning hair, sparse eyebrows and eyelashes, and dry and fragile skin and nails. The anti-aging market provides remedies and solutions directed mainly to enhance facial beauty. It is desired to have "anti-aging" products that affect the molecular and cellular processes contributing to the aging process, and provide additional functional benefits, not just cosmetic effects.

The mid-50s "free radical theory of aging" correlates cumulative oxidative damage with the degree of aging. Oxidative stress, (or the imbalance between reactive oxygen species (ROS) creation and the ability to detoxify ROS and repair the resulting damage) is increased with age and with UV exposure, while the antioxidant response of the aging cells slows with the accumulation of mutations. ROS induce inflammatory processes and immune-suppression, which further contribute to barrier damage and compromise skin integrity. Clinical data suggest that reducing oxidative stress contributes to skin health and wellness and reduces aging manifestations. It is desired to have an "anti-aging" skin care solution that not only reduces oxidative stress, but also enhances the endogenous antioxidant response of the aging cells.

One of the more noticeable and unwanted signs of aging is skin pigmentary lesions. The brown spots that appear on UV-exposed skin areas ("age spots") are one such pigmentary problem. Additionally, age-induced white, hypo-pigmented spots (idiopathic guttate hypomelanosis, IGH) also appear on sun-exposed, aged skin areas, and signal the undesired "old" look. These affected areas may stop making melanin at all, causing them to completely lose pigment, resulting in unsightly, but benign lesions. IGH lesions are commonly found in more than 50% of older and elderly individuals (aged>40 years), and about 30% of the individuals develop their initial IGH lesions prior to 20 years of age.

There is no treatment available for the spotted loss of skin pigmentation such as in IGH. It is desired to have a topical treatment that could preserve the natural skin color, or prevent, or slow, or reduce or reverse spotty skin pigment loss in the pigment-losing areas of the skin such as in IGH. It is more desired to have such a treatment as a single and affordable topical treatment for daily skin care. Such a treatment should provide solutions to spotty skin pigment loss with minimal or no irritation and few or no negative side effects, and should further provide other desired skin health, wellness and beautifying benefits.

IGH should not be confused with vitiligo, which is a skin depigmenting disease. Vitiligo is a disorder in which white, non-pigmented patches of skin appear on different parts of the body. The vitiligo lesions are large patches, they expand rapidly, and they are not related to sun exposure or aging. Vitiligo may arise from autoimmune, genetic, neural, or viral causes, as well as from oxidative stress. In some cases, vitiligo spreads slowly, over many years, however, in other cases the spreading occurs very quickly. Some reports associate the increase in white patches with physical or emotional stress. The most commonly prescribed treatment for vitiligo is a potent or super-potent topical corticosteroid. Unfortunately, only about 45 percent of patients regain some skin color following months of this treatment. Light therapy is very ineffective, and PUVA therapy does not provide satisfactory results as well.

It is desired to have a topical treatment that could preserve the natural skin color, or prevent, or slow, or reduce or reverse pigment loss in vitiligo. It is more desired to have such a treatment as a single and affordable topical treatment for daily skin care. Such a treatment should provide solutions to vitiligo with little or no irritation and few or no negative side effects, and should further provide other desired skin health, wellness and beautifying benefits.

Geriatric skin (generally referred to the skin of individuals 65 years old or older, but the age can vary due to numerous factors) is significantly aged and therefore very fragile. It is thin and dry, very itchy, easily bruised and predisposed to wounding, tearing and infections, therefore affecting both health and quality of life. In the elderly skin, the aging processes continue and magnify. The amount of inflammatory infiltrate is increased, wound healing and immune responses are delayed, thermoregulation is compromised and sweat and sebum production are decreased. The cumulative effects of life-long environmental exposure further enhance functional skin aging in the elderly. These include not only UV exposure, pollution and smoke, but also factors like air conditioning, heating and hot water use. Diseases, and in particular diabetes, immune disorders, cardiac diseases, renal or hepatic failure, malignancies and infections enhance the skin aging process as does the prolonged use of medications like steroids, anticoagulants, blood thinners, immune-modulators and cancer therapies. Slowness and life style changes further contribute to dehydration and reduced skin nutrition, enhancing the dryness and fragility of the elderly skin, and contributing to an increase in "little injuries" and their consequences. Interestingly, it was suggested that most of the elderly skin changes associated with aging are due to intrinsic aging rather than photodamage or lifestyle.

The major needs of geriatric skin are not related to facial beauty, but to the health and well-being of body skin. What is needed is to reduce dryness and itchiness, to reduce the amount and the severity of skin injuries, to reduce skin tears, reduce hematomas, enhance the healing time of minor injuries, reduce the rate of infections, and the like. Unfortunately, there are few, if any, consumer products dedicated to these geriatric skin needs. Geriatric skin could benefit from enhancing its biological properties and reducing undesired attributes such as pruritis or fragility in a way superior to the use of moisturization alone. It is desired to have a topical treatment that could prevent, slow, reduce or reverse skin aging processes in geriatric skin. It is more desired to have such a treatment as a single and affordable topical treatment for daily care. Such a treatment should provide solutions to geriatric skin needs, with little or no irritation and few or no negative side effects to the fragile skin, and should further provide other desired health, wellness and cosmetic benefits. It is further desired to have such a single topical treatment that does not require a pharmaceutical prescription.

Elderly patients experience common nail changes and dystrophies that induce pain, affect daily activities, and are of cosmetic concern. With age, nails may become brittle and prone to breaking, may become clubbed (a significant shape-change with very rounded nails), or may be discolored. Unfortunately, there are no consumer products dedicated to elderly nail care, or to the general health and wellbeing of the nails. It is desired to have products to enhance the biological properties of the nails and their surrounding skin and cuticle, and to reduce undesired properties associated with nail aging. It is more desired to have such a product as a single and affordable topical treatment for daily care. Such a treatment should provide solutions to geriatric skin needs, with little or no irritation and few or no negative side effects to the fragile skin, and should further provide other desired health, wellness and cosmetic benefits. It is further desired to have such a single topical treatment that does not require a pharmaceutical prescription.

SUMMARY

The present disclosure features compositions for the topical delivery of a natural extract(s) product (e.g., to a mammal in need thereof, such as a human) comprising a natural product(s) such as, but not limiting to, a botanical extract, an algae extract, a yeast extract, a fungi extract or a microorganism extract, or a fraction(s) of such extract, or a combination(s) thereof (collectively defined as "natural extract"). In one instance, the natural extracts of this disclosure (1) contain active, non-denatured catalase and/or glutathione peroxidase, or (2) have a catalase-like activity (e.g. degrading or eliminating hydrogen peroxide), or (3) have a catalase-enhancing activity (e.g. enhancing gene expression, protein translation or other activity that leads to an increase in hydrogen peroxide degradation or elimination), or (4) have a catalase stabilizing activity, or a combination of one or more such activities (collectively defined as "catalase-related activity" or "catalase-like activity"). In another embodiment, the natural source of this disclosure (e.g. botanical, plant, algae, yeast, fungi or microorganism) could be grown with, or enriched with, or supplemented with, or engineered for producing, or combined with the L-methionine, or the natural extracts themselves could be combined with L-methionine.

In one embodiment the present disclosure describes a natural extract and a pharmaceutical or a cosmetic carrier. In yet another illustration, the compositions of this disclosure further comprise of delivery system(s), or vehicle(s), or stabilizing system(s) that enable to maintain an active catalase-related activity, and deliver such an activity into the skin, the nail or the hair follicles.

The compositions described in this disclosure could be used for skin, hair and nail care, to provide skin, scalp, hair and nail with health and wellness benefits, and to provide skin, scalp, hair and nail with anti-aging and with geriatric skin benefits. In yet another feature, the compositions described in this disclosure could be used to reduce the visibility of the signs of skin, scalp, hair and nail aging and the signs of geriatric skin.

The present disclosure also features a method of reducing the hair graying process of a mammal, said method comprising the step of applying a composition described herein to the scalp or to other desired skin areas with hair or to non-glabrous skin. Gray hair is defined as the hair that has changed its color from the original natural hair color due to biological processes such as aging, chemical exposure, environmental exposure, nutritional exposure, medicine exposure and the like, and is of reduced color, or achromatic color, or an intermediate between white and black that is lighter than the original natural hair color. Human non-glabrous skin is defined as all human skin areas that are hairy, or that can grow hair or that can contain hair follicles. Non-glabrous skin refers to all external skin that is not naturally hairless, and excludes only the skin found on the ventral portion of the fingers, palms, soles of feet, lips, labia minora, and glans penis. Reducing hair graying includes, but is not limited to the preservation of the natural color of the hair, or to reducing the quantity or quality of loss of the natural hair color or to the slowing, reducing, or reversing the process of hair graying, or to preventing hair graying, or to reducing the visibility of hair graying.

The compositions described in this disclosure could also be used to preserve the natural color of the skin, or to slow, or to reduce, or to delay, or to reverse the loss of pigment on the skin or the uneven decay in the natural color of the skin, or to reduce the visibility of hypo-pigmentary skin lesions (including, but not limiting to, pigment-loss lesions, "white spots", IGH and vitiligo lesions). Such lesions include, but are not limited to, age-induced white, or lighter than the natural skin color, or hypo-pigmented spots (e.g. idiopathic guttate hypomelanosis, IGH), and disease-induced pigmentary loss (e.g. vitiligo). The present disclosure also describes a method of reducing the appearance of non-pigmented skin areas of a mammal, said method comprising the step of applying the above compositions to the desired skin areas.

In one aspect, the present disclosure relates to methods of preserving the natural color of the hair, or slowing the decay in the natural pigment production of the hair follicle, or delaying, or slowing, or reducing the severity of hair graying, or reducing the appearance of hair graying, by applying a composition containing a safe and effective amount of a natural extract. In another aspect, the natural extract could be supplemented with, enriched with or combined with L-methionine.

In another aspect, the present disclosure relates to methods of preventing the decay in the natural pigment production of the hair follicle and reducing the appearance of hair graying, by applying a composition containing a safe and effective amount of a natural extract. In one aspect the natural extract could be supplemented with, enriched with or combined with L-methionine.

Yet in another aspect, the present disclosure relates to methods of partially or completely reversing the decay in the natural pigment production of the hair follicle and reducing the appearance of hair graying, by applying a composition containing a safe and effective amount of a natural extract. In one aspect the natural extract could be supplemented with, enriched with or combined with L-methionine.

In another aspect, the present disclosure features a product including a composition comprising a natural extract and instructions directing the user to apply the composition to the hair, scalp, or other skin areas with hair (non-glabrous skin), in order to preserve the natural hair color, or slow, or prevent or reverse the decay in the natural pigment production of the hair follicle, or slow, or prevent or reverse the appearance of hair graying. Such hairy skin areas include, but are not limited to the scalp, head, eyebrows, eyelashes, beard, mustache, chest, back, arms, legs and the like.

Yet in another aspect, the present disclosure features a method of promoting a product including a composition containing a natural extract by directing the user to apply said composition to the hair, scalp or hairy skin areas, or non-glabrous skin, in order to preserve the natural hair color, or to slow, or prevent or reverse the decay in the natural pigment production of the hair follicle, or to slow, or prevent or reverse the appearance of hair graying.

In another aspect, the present disclosure relates to methods of preserving the natural color of the skin, or of slowing the uneven decay in the natural pigment production of the aging skin, or of delaying, or slowing, or reducing the severity or the visibility of loss-of-pigment lesions (e.g. IGH, "white spots", or vitiligo), by applying a composition containing a safe and effective amount of a natural extract. In another aspect the present disclosure relates to methods of preserving the natural color of the skin, or of slowing the development of pigmentary skin loss, or of delaying, or slowing, or reducing the severity of mottled pigment loss, by applying a composition containing a safe and effective amount of a natural extract. In yet another aspect, the natural extract could be supplemented with, enriched with or combined with L-methionine.

In another aspect, the present disclosure relates to methods of preserving the natural color of the skin, or of preventing the decay in the uneven pigment production of the skin, or of reducing the appearance of non-pigmented skin lesions, by applying a composition containing a safe and effective amount of a natural extract. In yet another aspect, the natural extract could be supplemented with, enriched with or combined with L-methionine.

Yet in another aspect, the present disclosure relates to methods of partially or completely reversing the uneven decay in the pigment production of the skin, or reducing the appearance of non-pigmented skin lesions, by applying a composition containing a safe and effective amount of a natural extract. In yet another aspect, the natural extract could be supplemented with, enriched with or combined with L-methionine.

In another aspect, the present disclosure features a product including a composition comprising a natural extract and instructions directing the user to apply the composition to the affected or desired skin areas, in order to preserve the natural skin color, or to slow, or prevent, or reverse the decay in the production of pigment in the skin, or to slow, or prevent or reverse the appearance of non-pigmented skin lesions.

Yet in another aspect, the present disclosure features a method of promoting a product including a composition containing a natural extract by directing the user to apply said composition to the affected or desired skin areas, in order to preserve the natural color of the skin, or to slow, or prevent or reverse the decay in the pigment production of the skin, or to slow, or prevent or reverse the appearance of non-pigmented skin lesions.

In yet another instance, the present disclosure relates to methods of enhancing skin, scalp, hair and nail health and wellness, beautifying the skin, hair and nail, providing anti-aging benefits, or enhancing the biological properties and the health and wellness of elderly skin, by applying a composition containing a safe and effective amount of a natural extract to the skin (both glabrous and non-glabrous areas) to enhance skin health, wellness and appearance. In yet another aspect, the natural extract could be supplemented with, enriched with or combined with L-methionine. In yet another aspect, the anti-aging benefits of the compositions of this disclosure would include the desired structural, functional and visual effects on wrinkles, sagging, "age spots", and other signs and symptoms of facial skin aging. Yet in another aspect, the geriatric skin benefits of the compositions of this disclosure would include enhancing the structural and functional properties of elderly nails, facial-, scalp- and body-skin, reducing dryness of facial, scalp and body skin, reducing skin pruritis, reducing skin and nail fragility, reducing the quantity and severity of hematomas, reducing the quantity and the severity of skin tears and other skin wounds, reducing skin infections, and enhancing wound healing of skin wounds. Body skin is referred to all human skin areas, including nails, and in particular to the skin of the arms, hands, fingers, legs and feet.

In another aspect, the present disclosure features a product including a composition comprising a natural extract and instructions directing the user to apply the composition to the affected or desired skin, scalp and nail areas, in order to enhance skin, scalp and nail health and wellness, to reduce the signs of skin aging, or to combat the reduced qualities and problems of geriatric skin.

Yet in another aspect, the present disclosure features a method of promoting a product including a composition containing a natural extract by directing the user to apply said composition to the affected or desired skin, scalp and nail areas, in order to enhance skin, scalp and nail health and wellness, to reduce the signs of skin, scalp, hair and nail aging, or to combat the reduced qualities and problems of geriatric skin.

Other features and advantages of the present disclosure will be apparent from the detailed description of the disclosure and from the claims. It is believed that one skilled in the art can, based upon the description herein, utilize the present disclosure to its fullest extent. The following specific examples are to be construed as merely illustrative and not limitative of the remainder of the disclosure in any way whatsoever. Unless defined otherwise, all technical and scientific terms used herein have the same meaning as commonly understood by one of ordinary skill in the art to which the disclosure belongs. Also, all publications, patent applications, patents, and other references mentioned herein, are incorporated herein by reference. Unless otherwise indicated, a percentage refers to a percentage by weight (e.g. % (w/v)).

DETAILED DESCRIPTION

The present disclosure relates to the recognition that certain natural extracts are very effective in the elimination of hydrogen peroxide, and therefore they could be used for preserving the natural color of skin and hair, or for preventing, or slowing, or reducing or reversing the appearance of hair graying or depigmented skin lesions, or for reducing the general signs of skin, scalp, hair and nail aging and the specific signs of geriatric elderly skin.

Amor Seco (*Desmodium Adscendens, Desmodium coeruleum, D. caespitosum, D. glaucescens, D. heterophyllum, D. oxalidifolium, D. triflorum, Hedysarum adscendens, H. caespitosum, Meibomia adscendens*) is a tree species of the Acalyphoideae, native to South America. It is locally known as tamanqueiro, tapiá or amor seco. It grows preferentially in riparian forests, reaching a height of 10-20 m. It is essentially an evergreen, though in the hot summer months there is a more pronounced changeover of leaves, and branches are denuded to some extent. Amor Seco leaf powder is produced from Amor Seco leaves, which are cleared of foreign material and are milled and grinded. The powder is used as a food additive (see e.g. http://www.nutricargo.com/herb-powders/amor-seco-powder).

It was unexpectedly found that Amor Seco leaf powder has hydrogen peroxide degrading activity (see Example 1). Moreover, exposure of human keratinocytes to Amor Seco leaf powder results in an enhancement of the endogenous cellular activity of the keratinocytes in degrading or eliminating hydrogen peroxide (see Example 2). Additionally, Amor Seco leaf powder exhibited strong activity against hydrogen-peroxide-induced oxidative stress (example 3). These results suggest that Amor Seco leaf powder could be used topically, on skin, scalp, nail and hair, to reduce hydrogen peroxide concentration, and therefore to be useful in this disclosure. The topical use of Amor Seco leaf powder should slow, delay and reduce the progression of hair graying. Similarly, the topical use of Amor Seco leaf powder should reduce the visibility of depigmented skin lesions and could reduce the signs of skin, scalp, hair, and nail aging and enhance elderly skin properties. It is expected that other plants of the family Fabaceae, and not only those from the genus *Desmodium*, would have similar biological properties and could also be used in a similar manner.

Yacón (*Smallanthus sonchifolius*, Syn.: *Polymnia edulis, P. sonchifolia*, Peruvian ground apple) is a perennial plant traditionally grown in the Northern and Central Andes from Colombia to Northern Argentina for its crisp, sweet-tasting tuberous roots. Commonly called "jicama" in Ecuador, yacón is sometimes confused with this unrelated plant. Yacón is actually a close relative of the sunflower and Jerusalem artichoke.

It was unexpectedly found that Yacón leaf powder has hydrogen peroxide degrading or eliminating activity (see Example 1). Moreover, exposure of human keratinocytes to Yacón leaf powder results in an enhancement of the endogenous cellular activity of the keratinocytes in degrading or eliminating hydrogen peroxide (see Example 2). Additionally, Yacón leaf powder exhibited strong activity against hydrogen-peroxide-induced oxidative stress (Example 3). These results suggest that Yacón leaf powder could be used topically, on skin, scalp, nail and hair, to reduce hydrogen peroxide concentration and provide beneficial effects. The topical use of Yacón leaf powder should slow, delay or reduce the progression of hair graying. Similarly, the topical use of Yacón leaf powder should reduce the visibility of depigmented skin lesions, and could reduce the signs of skin, scalp, hair, and nail aging and enhance elderly skin properties. It is expected that other plants of the family Asteraceae, and not only those from the genus *Smallanthus*, would have similar biological properties and could also be used in a similar manner.

The red microalgae *Porphyridium* (Genus: *Porphyridium*, including, but not limiting to *Phytoconis purpurea* Bory de Saint-Vincent, 1797, *Porphyridium* Nageli, *Byssus purpurea* Lamarck, *Olivia cruenta* S. F. Gray, *Olivia cruenta* S. F. Gray, *Porphyridium cruentum* (S. F. Gray) Nägeli, *Porphyridium marinum* Kylin, *Sarcoderma sanguineum* Ehrenberg, *Porphyridium* sp. UTEX 637 or a strain derived from *Porphyridium* sp. UTEX 637, *Porphyridium cnientum* UTEX 161 or a strain derived from *Porphyridium omentum* UTEX 161, *Porphyridium aerugineurn* or a strain derived from *Porphyridium aerngineum*, *Porphyridium sordidum* or a strain derived from *Porphyridium sordidum*, or *Porphyridium purpureum* or a strain derived from *Porphyridium purpureum*) is a unicellular red (Rhodophyta) microalga, with cells of 10-20 μM in diameter. Its habitats include fresh water, brackish water, sea water and soil, and it can grow under harsh climate conditions and high UV exposure.

During the processing of the algae polysaccharide, the algae biomass (the algae cells) is removed while the secreted polysaccharide is retained. The precipitated algae biomass is sometimes considered a waste product, which is discarded during the production of the polysaccharide. The algae is rich in xanthine derivatives, which are sometimes extracted from the biomass for nutritional uses. In other times the algae pigments are extracted from the biomass.

It was unexpectedly found that dried *Porphyridium* biomass has hydrogen peroxide degrading and eliminating activity (see Example 1). Moreover, exposure of human keratinocytes to dried *Porphyridium* biomass results in an enhancement of the endogenous cellular activity of the keratinocytes in degrading and eliminating hydrogen peroxide (see Example 2). These results suggest that dried *Porphyridium* biomass could be used topically, on skin, scalp, nail and hair, to reduce hydrogen peroxide concentration and provide beneficial effects. The topical use of dried *Porphyridium* biomass should slow, delay and reduce the progression of hair graying. Similarly, the topical use of dried *Porphyridium* biomass should reduce the visibility of depigmented skin lesions, and could reduce the signs of skin, scalp, hair, and nail aging and enhance elderly skin properties. It is expected that other plants of the family Porphyridiaceae, or of the Phylum Rhodophyta and not only those from the genus *Porphyridium*, would have similar biological properties and could also be used in a similar manner. Non-limiting examples of other red microalgae suitable for this disclosure include the unicellular algae of the Bangiophyceae, Florideophyceae, Goniotrichales, *Dixoniella grisea*, or other member of the Rhodophyta.

The precise concentrations, effects of the composition and methods of this disclosure will vary with the area being treated, the age, health and skin and hair type of the end user, the duration and nature of the treatment, the specific composition employed, the particular condition being treated, the particular cosmetically- or pharmaceutically-acceptable carrier utilized, and like factors.

The present disclosure describes a natural extract(s) or their fraction(s), or combination(s) thereof (1) containing active, non-denatured catalase, or (2) having a catalase-like activity, or (3) having a catalase-enhancing activity, or (4) having a catalase-stabilizing activity, or mixtures thereof. The natural extract described in this disclosure can be, but is not limited to, a plant extract, an algae extract, a yeast extract, a fungi extract, a microorganism extract, or a fraction(s) of such extract(s), or combinations thereof.

The natural extracts of this disclosure are aqueous. Aqueous extracts are materials that were extracted by any solvent consisting totally or partially of water, including, but not limited to water itself, aqueous/alcoholic solvents in any proportion, or solvents comprising water and a compound such as propylene glycol, in any proportion. The aqueous extract could be in a liquid form or could be dried out to a solid form.

When the aqueous extract is dried

In one instance, an enhancement of catalase production within the natural source is achieved by (1) selecting relevant genetic variants, or (2) using genetic engineering technologies, or (3) controlling a timed and selective exposure (e.g. continuous, pulsed, at a defined growth phase) to hydrogen peroxide, or (4) controlling a timed and selective exposure to different wavelengths (e.g. UV, blue, or others), or (5) providing certain ingredients (e.g. chemicals, nutritional agents) that affect the growth or the biological properties of the natural source, before collecting the natural source for extraction, or combinations thereof.

In another instance, the natural source (1) could be grown under nutritional conditions that enrich for L-methionine, or (2) could be grown under nutritional conditions that enhance the production of L-methionine, or (3) could be supplemented with L-methionine during growth, or (4) could be engineered to produce or retain L-methionine, or (5) could be combined with L-methionine during the preparation and processing of the natural extract. The L-methionine enriched extract could be used in all the compositions and methods disclosed herein, and is expected to have superior effects in reducing hydrogen peroxide concentrations in skin, scalp, hair and nail. In one example the fertilization of plants is performed with a micronutrient composition that includes high levels of L-methionine. Another example relates to the enrichment of the growth medium of algae, fungi, yeast and other microorganisms with about 0.1-100 mM L-methionine, which can lead to increased methionine in the extracts prepared from these materials. In addition or as an alternative, the natural extract (e.g. Amor Seco leave powder, Yacón leave powder or dried *Porphyridium* biomass, or their aqueous extracts) can be combined with 0.1-100 mM of L-methionine, at any stage of the natural extract production and processing.

The effective concentration of L-methionine in the composition should be about the same as the concentration of hydrogen peroxide within the affected tissue (e.g. the graying hair follicle, the vitiligo lesion, the elderly skin, and the like). This concentration varies with the age, gender, skin type and hair type of the individual, and with their specific need (e.g. hypo-pigmented lesions, gray hair, elderly skin, and the like). Lower concentrations (high micromolar range) would be effective for geriatric skin, while higher concentrations (low milimolar range) would be required for affecting gray hair and hypo-pigmentary skin lesions.

In another instance, the natural extracts of this disclosure are non-denatured, and contain stable and active proteins like the catalase enzyme or the glutathione peroxidase enzyme. "Denaturation" is defined in the Bantam Medical Dictionary (1990 edition) as "the change in the physical and the physiological properties of a protein, that are brought about by heat, X-rays or chemicals. These changes include loss of activity in the case of enzymes". What is meant by "non-denatured product" is a natural product in which the processing for the derivation of such product (e.g., the temperature, extraction media) did not eliminate its specific hydrogen peroxide elimination activity.

In yet another aspect, extracts of this disclosure could be further purified, or concentrated or fractionated or combined to increase the content of the catalase enzyme or the glutathione peroxidase enzyme or the catalase-like activity.

Awareness to environmental concerns has increased, and "green" considerations are incorporated into products and disclosures. In one instance, the natural sources of this disclosure would consist of unused or "wasted" natural products. Examples for such sources include, but are not limited, to leaves and stems that are not collected in the field, or are collected and then separated, when fruits, vegetables, roots and grains are harvested, and might be otherwise discarded or provided for animal feed. Other examples include plants parts that are removed during food processing, like legume pods or fruit and vegetable peels. Another example includes botanical parts that are removed during the processing or production of specific botanical products, such as the algae biomass that is removed during the production of the algae polysaccharide.

Extracts of this disclosure can be tested for their hydrogen peroxide eliminating activity using colorimetric or spectrophotometric assays such as the Catalase Assay Kit of Cayman Chemical (#707002), the BioVision Inc. Catalase Activity Colorimetric/Fluorometric Assay Kit (#K773-100), The Sigma Aldrich Enzymatic Assay of Catalase (EC 1.11.1.6) kit, the Amplex/-E Red Catalase Assay Kit (#A22180) of Molecular Probes, or the like. Such assays are sensitive to detect pico units of catalase activity within samples. The catalase enzyme itself can also be detected and quantified within the extracts using standard procedures, however the existence of the protein does not guarantee its activity, and therefore the activity assays are preferred, and are used to define the natural extracts.

In another instance, the natural extracts of this disclosure contain catalase-like activity, namely the ability to degrade or eliminate hydrogen peroxide, directly or indirectly, without containing an intact catalase or glutathione peroxidase enzyme. In one aspect, such extracts could be further concentrated, or purified, or fractionated, or combined to increase the content of the catalase-like activity. In another aspect, such extracts could be tested for their hydrogen peroxide eliminating activity using similar assays to those describe above, as such assays are measuring the reaction products and not the enzyme concentrations. Such extracts could be defined, therefore, by their hydrogen peroxide eliminating activity.

Topically applied agents of relatively large molecular weight have the potential to reach pharmacologically active concentrations at the hair bulb, if properly formulated with adequate delivery vehicles. The delivery occurs via the junction of the internal and external root sheath, and the higher molecular weight molecules are confined to the follicular structures immediately surrounding the hair shaft. (*J. Pharm Sci.* 1997 86(9):1022-9. Description of the intra-follicular delivery of large molecular weight molecules to follicles of human scalp skin in vitro. Lieb L M, Liimatta A P, Bryan R N, Brown B D, Krueger G G). However, it is desired sometimes to have active ingredients of smaller molecular weight delivered to the hair follicles, or directly to the skin, to increase and enhance their effective concentrations and their efficacy. In yet another example, the natural extracts containing catalase-like activity of this disclosure could be size fractionated and selected, and then concentrated, or combined, to increase the concentration of smaller molecular weight ingredients with the desired activity within the composition. In one aspect, the molecular weight of the ingredients having the desired activity is smaller than that of catalase. In another aspect, the molecular weight of the ingredients having the desired activity is smaller than 1 kDa. The size of ~0.5 kDa is considered the largest for passive skin penetration (Bos J D, Meinardi MMHM. The 500 Dalton rule for the skin penetration of chemical compounds and drugs. *Exp Dermatol.* 2000 9:165-16)]. In yet another aspect, the molecular weight of the ingredients having the desired activity is smaller than ~0.5 kDa.

The natural extract of this disclosure could enhance the gene expression, or the protein translation, or the stability, or the activity of the endogenous catalase enzyme or the endogenous glutathione peroxidase enzyme in the skin, or the nail, or the hair follicle. In one aspect, such extracts could be further concentrated, or purified or fractionated or combined to enhance such an activity. In one aspect, such extracts could be defined by their hydrogen peroxide eliminating activity.

In yet another example, extracts of this disclosure that enhance the expression, or the stability, or the activity of the endogenous skin, scalp, nail, or hair follicle catalase enzyme and/or glutathione peroxidase enzyme, could be size fractionated and selected, and then concentrated, or combined, to increase the concentration of smaller molecular weight ingredients with the desired activity in the composition. In one aspect, the molecular weight of the ingredients that enhance the expression, or the stability, or the activity of the endogenous skin, nail, scalp or hair follicle catalase and/or glutathione peroxidase enzyme is smaller than that of catalase. In another aspect, the molecular weight of the ingredients that enhance the expression, or the stability, or the activity of the endogenous skin or hair follicle catalase and/or glutathione peroxidase enzyme is smaller than 1 kDa. In yet another aspect, the molecular weight of the ingredients that enhance the expression, or the stability, or the activity of the endogenous skin or hair follicle catalase and/or glutathione peroxidase enzyme is smaller than 0.5 kDa.

The natural extracts of this disclosure can be evaluated for their catalase and/or glutathione peroxidase enhancing activity in skin, scalp, hair or nail or in their relevant in vitro systems. Such in vitro systems include, but are not limited to epidermal, or dermal, or epidermal-dermal skin constructs that can be obtained commercially, e.g. from MatTek corporation, monolayers of melanocytes, epidermal keratinocytes, dermal fibroblasts or follicular keratinocytes that can be obtained commercially, e.g. from ATTC, skin explants with and without hair that can be obtained from e.g. human and animal biopsies, cultured hair plugs, and the like. An example of such an assay includes the incubation of the biological samples with and without the extracts of this disclosure, using a range of safe and effective concentrations, for different time points (e.g. 24, 48 and 96 hours). The biological samples can be homogenized and tested for hydrogen peroxide elimination activity using the assays described above, or they can be tested for irritation biomarkers, sensitization biomarkers, inflammatory responses, anti-oxidant responses and the like using known procedures. Additionally, they can be tested for the enhanced expression or stability of the endogenous catalase and/or glutathione peroxidase enzyme, or of other cellular anti-oxidant enzymes, using standard molecular procedures. Additionally, the biological samples can be challenged (e.g. with UV irradiation or hydrogen peroxide exposure) and their viability and their biological responses and catalase and/or glutathione peroxidase expression and activity can be evaluated using known and validated assays for e.g. catalase and/or glutathione peroxidase expression or activity, irritation, sensitization, inflammatory responses, anti-oxidant responses and the like. Viability can be evaluated with e.g. a standard MTT assay. Irritation and inflammatory responses can be evaluated e.g. by measuring the release of inflammatory cytokines such as IL-1 alpha into the culture media, using standard ELISA techniques. Anti-oxidant responses can be measured with standard assays e.g. using ABTS (trolox equivalent) or DPPH kits. Catalase and/or glutathione peroxidase expression and stability can be evaluated using standard techniques such as QPCR or protein immunereactivity over time.

The novel compositions of this disclosure contain aqueous natural extracts, which might be present in many forms such as of a fluid or a solid. In one example, the aqueous natural product is in the form of a suspension. One way to make the natural suspension is to soak the fresh or dry natural sources in a liquid (e.g. water) for from about 10 minutes to several hours, and after they were fully hydrated to press, or grind them, to allow the ingredients to be extracted. Procedures such as pressure disruption, sonication and milling (e.g., jet milling and ball milling, sometimes performed under cold or freezing conditions) can be used instead of grinding, to break down the biological material for improved extraction. The suspension may be filtered to remove any residual parts. In one example the suspension is filtered using a 0.2 micron pore size filter. The natural suspension could be dried by e.g. tray drying, spin drying, rotary drying, spin flash drying, or lyophilization.

Another example is to press the natural sources and collect the "juice" created by the pressing of the natural material. After collection, the suspension may be filtered to remove any residual parts. In one instance the suspension is filtered using a 0.2 micron pore size filter. The natural suspensions and solutions used in this disclosure can use fresh natural sources, or may be made from dry, powdered natural sources and liquid. The powder is milled (e.g. by pressure disruption, sonication, jet milling or ball milling and the like) from the natural sources (e.g. botanical parts, algae, fungi or microorganism cultures and the like) and may also be dried (e.g. lyophilized, spin-dried, spray dried, tray dried, spin flash dried, freeze-dried and the like) and the resulting powder may or may not be filtered. In one example the suspension or solution is filtered using a 0.2 micron pore size filter. Such prepared suspension or solutions may have from about 0.01 to about 90% by weight dry powder.

Another example is the use of natural extract powder, made from, e.g. lyophilized, spray dried or freeze-dried suspension as described above and the like, with the addition of liquid and with or without filtration or homogenization.

Other known methods of extraction could also be used to create the active ingredients used in this disclosure. For example, but not limited to, the active ingredients could be extracted from ground natural sources using ethanol/water mixtures, followed by the removal of the ethanol from the extract, in such ways that the specific catalase and/or glutathione peroxidase activity or catalase-related activity of the preparation will be retained. Known methods of fractionation could be used to separate and concentrate the desired activities of this disclosure, or to size fractionate the natural extract, or to eliminate inhibitory or undesired activities.

In one example, the natural extracts of this disclosure could be produced using electro-kinetic potential (Zeta) fractionation and separation (e.g. with the Zeta Fraction™ Technology (http://www.sc.akzonobel.com/en/personalcare/Pages/zeta-fraction.aspx)). Zeta Fraction technology can selectively isolates intracellular components from biological sources, e.g. from plants "juices", without the use of external solvents for separation. Targeted fractions with active catalase and/or glutathione peroxidase, or with catalase-like activity, could be mechanically separated based on their electro-kinetic (zeta) potential, to be used in compositions of this disclosure. The zeta fractions could be further processed (e.g. filtered, dried, combined) as described above.

Yet in another example, the fresh or dry natural source of this disclosure could be grinded or milled as described above, suspended in a liquid (e.g. water) and then undergo a mechanical homogenization, or a particle-size reduction (e.g. by sonication, or shear mixing, or homogenization, or any other known semi solid processing, sometimes performed under cold or freezing conditions) to create a homogenate (so that the cells or biomass of the natural source are broken or disrupted). The resulting suspension could then be separated (e.g. by centrifugation of e.g. 500-1,000 RPM for 10 minutes, or by similar procedures), and the supernatant could be further size-selected (e.g. for particles of the size of 0.2 micron or smaller, e.g. by size filtration membranes, ultra-filtration and the like). The resulting suspension or solution of, e.g., 0.2 micron size particles or smaller could be used for the compositions of this disclosure "as is", or could be dried-out using standard procedures (e.g. lyophilized, spin-dried, spray dried, tray dried, spin flash dried, freeze-dried and the like) to create a more refined natural extract. All such processes should not create unreasonable heat that might reduce or eliminate the biological activity of the natural extract.

Cosmetic or Pharmaceutical Carrier

Useful compositions can include stabilization systems, which may include one or more preservatives, or one or more anti-oxidants, or one or more chelating agents, or combinations thereof. Preservatives are useful for substantially preventing microbial decomposition. Examples of preservatives include, but are not limited to phenoxyethanol, parabens and natural preservatives, and are known to the ones skilled in the art. Other examples of preservatives could be found on pages 1654-55 of the International Cosmetic Ingredient Dictionary and Handbook, eds. Wenninger and McEwen (CTFA, 7th ed., 1997), hereinafter referred to as the "Cosmetic Handbook." The composition may comprise from about 0.01% to about 20%, by weight (sometimes more preferably, from about 0.5% to about 5%, by weight) of preservative. Microbial contamination can also be eliminated by gamma irradiation, or electron-beam irradiation, or X-ray irradiation and the like, by microfiltration, or by other standard procedures (e.g. brief heat treatments) that do not result in the elimination of the specific activity described in this disclosure.

Antioxidants and/or chelating agents may also be used to increase shelf life and stability of the compositions. Antioxidants may be added both for formulation stabilization and for biological efficacy. Antioxidant compounds and their derivatives include, but are not limited to, water-soluble antioxidants such as sulfhydryl compounds and their derivatives (e.g., sodium metabisulfite and N-acetyl-cystein), lipoic acid and dihydrolipoic acid, resveratrol, acetyl-cysteine (Iniferine®) or lactoferrin, and ascorbic acid and ascorbic acid derivatives (e.g., ascorbyl palmitate and ascorbyl polypeptide). Oil-soluble antioxidants suitable for use in the compositions of this disclosure include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this disclosure, include, but are not limited to, extracts containing flavonoids and isoflavonoids and their derivatives (e.g., genistein and diadzein), extracts containing resveratrol, extracts containing polyphenols and the like. Examples of such natural extracts include, but are not limited to, grape seed, tea, pine bark, Aloe Vera, propolis, or legume extracts. Small molecules with specific antioxidant activity, including, but not limiting to catalase mimetics, SOD mimetics, salem-Mn complexes (e.g. the EUK family of compounds), and the like, are also suitable for use in compositions of this disclosure. Other examples of antioxidants may be found on pages 1612-13 of the Cosmetic Handbook. The compositions of the present disclosure may comprises the antioxidant in an amount of from about 0.001% to about 20%, by weight (e.g., from about 0.01% to about 10% by weight) of the composition.

Chelating agents are also useful in assisting the stabilization of compositions. Examples of chelating agents include, but are not limited to EDTA and derivatives thereof (e.g., disodium EDTA and dipotassium EDTA), Iniferine lactoferrin, and citric acid. Other examples of chelating agents are listed on page 1626 of the Cosmetic Handbook. The compositions of the present disclosure may comprise the chelating agent in an amount of from about 0.001% to about 20%, by weight (e.g., from about 0.01% to about 10% by weight) of the composition.

Thickening agents (e.g., thickeners or viscosity enhancing agents) may be used to alter the viscosity of useful compositions. The desired viscosity of the composition will depend upon the intended use (e.g., as a shampoo, conditioner, mousse, cream, lotion, ointment, serum, spray, gel, stick, or the like). For example, in applications such as bath or wash products, the viscosity of the composition should be relatively low, similar to an aqueous solution. Application as a cream, lotion, or gel will have slightly higher viscosity (e.g., between about 100 cps and 100,000 cps). Thickening agents that can be added to the compositions of this disclosure to alter viscosity include polymers such as sepigels or polyacrylates (e.g., polyacrylamide, other carbomers) or polysaccharides (e.g. chitosan). Other examples of viscosity modifying agents are listed on pages 1692-97 of the Cosmetic Handbook. To achieve the appropriate viscosity, compositions of the present disclosure may comprise from about 0.01% to about 20%, by weight (e.g., from about 0.1% to about 5%, by weight) of a thickening agent.

Additional Cosmetically Active Agents

The compositions containing natural extracts can also contain other cosmetically active agents (e.g., a synthetic compound(s) or a compound(s) isolated from a natural source, or a natural extract(s) containing a mixture of compounds that has a cosmetic or therapeutic effect on the tissue). The useful compositions described herein may also contain other skin-, hair- and nail-beneficial agents in addition to the natural product(s). Examples of such agents include, but are not limited to, anti-inflammatory agents (such as corticosteroids, NSAIDs, or botanical extracts with anti-inflammatory activity such as Aloe Vera), anti-pruritic agents, topical analgesics, antioxidants (e.g. vitamin C and derivatives, vitamin E and derivatives, botanical extracts with antioxidant activity), agents with catalase-like or SOD-like activity (e.g. salem MN compounds such as the family of EUK agents), epidermal-, dermal- and follicular-regenerating agents and agents that enhance skin, hair and nail tissue regeneration agents (including e.g. retinoids, retinoid-derivatives, retinol, retinal, alpha hydroxy acids, co-enzyme-Q, growth factors, and others), antibiotics and anti-microbial agents, anti-mycotic agents, anti-yeast agents, anti-parasites, agents that enhance the immune system, dandruff-control and shine-control agents (including e.g. miconazole, ketoconazole, elubiol, itraconazole, coal tar and the like agents), detergents, surfactants, moisturizers, nutrients, vitamins, minerals, energy enhancers, hair or nail growth enhancing agents, agents that delay hair growth, agents for skin conditioning, odor-control agents (such as e.g. odor masking or pH-changing agents), deodorants, antiperspirants, colorants, pigments, color-masking agents, agents that enhance pigment production or pigment delivery (e.g. such as peptides, PAR-2 activators, MC1R ligands, alpha MSH and its mimetics, and the like), agents that enhance or inhibit pigment production, agents that affect methionine sulfoxide reductase activity (e.g. L-methionine, that could prevent the oxidation of methionine) and other agents that enhance skin, scalp, hair or nail wellness and beauty that are known to those of ordinary skill in the art.

The useful compositions described herein may also contain compounds that enhance the feel of the composition on the skin, scalp, hair or nail of the user. Examples of such compounds include, but are not limited to, oils, silicones (e.g., siloxane polymers such as dimethicone), polymers, polysaccharides, and skin-conditioning agents such as emollients, and humectants. Some examples of such skin conditioning agents may be found of pages 1656-1670 of the Cosmetic Handbook. In addition, the compositions useful herein can contain conventional cosmetic adjuvants, such as colorants (such as dyes and pigments), opacifiers (e.g., titanium dioxide), and fragrances, which are known to those skilled in the art in the field of this disclosure. The composition and formulations containing such compositions of the present disclosure may be prepared using methodology that is well known by an artisan of ordinary skill.

Forms

The compositions of this disclosure may be used, but are not limited to, with cosmetically or pharmaceutically accepted forms and carriers such as solutions, suspensions, emulsions (including microemulsions and nanoemulsions), lotions, creams, gels, sticks, sprays, ointments, cleansing liquids, washes, solid bars, shampoos, hair conditioners, nail polishes, nail strengtheners, pastes, foams, powders, mousses, shaving creams, shaving gels, wipes, patches, hydrogels, film-forming products, masks, liquid drops, muco-adhesives, and the like. The compositions of this disclosure may be packaged in a tube, a sealed packet, a jar, a pump, a bottle, a can, a pledget, a towelet, a dispenser, a wipe, a spray can or the like. An airtight or a light-blocking package (e.g. such as an aluminum tube, aluminum pocket, pump, or laminated tube), can also be used to further enhance product stability.

In one aspect, the compositions of this disclosure further comprise of delivery systems that enable to maintain an active catalase and/or glutathione peroxidase enzyme or catalase-related activity, and deliver the active ingredients, possibly including active proteins, into the hair follicles, or into the nail, or into the skin. Such delivery systems may include micro- and nano-particles, liposomes, aspasomes, organogels, niosomes, transferosomes, patches, micro- and nano-needles, micro- and nano-capsules, micro- and nano-sponges, films, polymers, and the like.

Compositions and Methods

The present disclosure features a method of reducing the hair graying process of a mammal, said method comprising the step of applying to the scalp or to other desired non-glabrous skin areas a safe and effective amount of the compositions of this disclosure. The frequency of the application will vary with the area being treated, the age, health, hair type and skin type of the end user, the duration and nature of the treatment, the specific composition employed, the particular cosmetically- or pharmaceutically-acceptable carrier utilized, and like factors. For example, in some instances the application would be periodic, while in other instances the application would be once or twice daily.

Additionally, the present disclosure features a method of reducing non-pigmented lesions on the skin of a mammal (e.g. of an age-induced or UV-induced pigment loss spots, or IGH, or vitiligo), said method comprising the step of applying to the skin areas a safe and effective amount of the compositions of this disclosure. The frequency of the application will vary with the area being treated, the age, health and skin type of the end user, the duration and nature of the treatment, the specific composition employed, the particular cosmetically- or pharmaceutically-acceptable carrier utilized, and like factors. For example, in some instances the application would be periodic, while in other instances the application would be once or twice daily. Additionally, the present disclosure also features a method of reducing the signs and symptoms of skin, scalp, hair and nail aging and enhancing the biological properties and the health and wellbeing of geriatric skin, said method comprising the step of applying to the skin, scalp, hair or nail areas in need a safe and effective amount of the compositions of this disclosure. The frequency of the application will vary with the area being treated, the age, health and skin type of the end user, the duration and nature of the treatment, the specific composition employed, the particular cosmetically- or pharmaceutically-acceptable carrier utilized, and like factors. For example, in some instances the application would be periodic, while in other instances the application would be once or twice daily.

As used herein, "safe and effective amount" means an amount of the composition sufficient to induce a desired effect on hair, nail or skin, but low enough to avoid serious side effects. The safe and effective amount of the composition will vary with the area being treated, the age, health, hair type and skin type of the end user, the duration and nature of the treatment, the specific composition employed, the particular cosmetically- or pharmaceutically-acceptable carrier utilized, and like factors.

It is understood that while the disclosure has been described in conjunction with the detailed description thereof, that the foregoing description is intended to illustrate and not limit the scope of the disclosure.

Example 1

This study evaluated the hydrogen peroxide breakdown activity of test agents. A Catalase assay kit was obtained from Cayman Chemical Co. (Ann Arbor, Mich.). The assay measures hydrogen peroxide elimination activity (e.g. catalase activity) using Purpald (4-amino-3-hydrazino-5-mercapto-1,2,4-triazole) as chromogen in a colorimetric assay. The testing involves the changes in optical density (OD) at 540 nm, which is proportional to the effective activity present in the sample based on the reaction with methanol in the presence of hydrogen peroxide. Purpald, used as chromogen, forms a bicyclic heterocycle with the formaldehyde produced, which upon oxidation changes from colorless to purple color.

Sample powders of the naturals were suspended in water or PBS at 5% (w/v), sonicated to break the material to sub-micron particles, homogenized, and centrifuged at 1,000 RPM for 10 min to remove insoluble material. Serial dilutions were prepared for each test material and mixed with methanol and hydrogen peroxide in assay buffer solution. Reaction was set for 20 minutes at room temperature. All samples were compared to assay buffer-treated samples (used as negative control). Catalase enzyme standard, derived from bovine liver, was used as positive control. Optical density changes at 540 nm were evaluated after addition of potassium hydroxide, Purpald and potassium periodate.

The results of this study are shown in Table 1. These results show that the dry leave powders of Amor Seco and Yacon and the dried *Porphyridium* biomass possess high hydrogen peroxide eliminating activity.

As a reference and for comparison, the literature (Nadira Binte Samad, Trishna Debnath, Michael Ye, Abul Hasnat, Beong Ou Lim. In vitro antioxidant and anti-inflammatory activities of Korean blueberry (*Vaccinium corymbosum* L.) extracts. *Asian Pac J Trop Biomed* 4(10): 807-815 (2014)) refers to two Korean blueberry (*Vaccinium corymbosum* L.) leaf extracts that are known to have strong antioxidant activities. These extracts were documented to have catalase activity of up to 0.67 nmol/min/ml at 0.33% (w/v). In contrasts, the natural extracts of this disclosure, at a lower (0.1% w/v) concentration, had their activity ranges from 1.5-2.5 nmol/min/ml.

hydrazino-5-mercapto-1,2,4-triazole) as chromogen in a colorimetric assay. The testing involved the changes in optical density (OD) at 540 nm, which is proportional to the effective activity present in the sample based on the reaction with methanol in the presence of hydrogen peroxide. Purpald, used as chromogen, forms a bicyclic heterocycle with the formaldehyde produced, which upon oxidation changes from colorless to purple color. Sample powders of the natural test agents were suspended in phosphate buffer (1×PBS) at 5% w/v, and were homogenized by sonication. Following a 1,000 RPM spin for 10 minutes, the supernatants were sterilized by filtration using a 0.2 µm syringe filter, as described in Example 1. The samples (sonicated filtered supernatants of the 5% suspensions) were then serially diluted to the desired test concentrations. Primary normal human epidermal keratinocytes (NHEKs) were seeded on 6-well plates and cultured for 24 hours. Subsequently, cells were treated with or without test materials, at 0.005, 0.05 and 0.5% (concentrations refer to the original 5% suspensions) in culture media, once daily, for 3 days. Cells were harvested on the $4^{th}$ day and then lysed and total protein concentrations in the lysates were measured using the BSA-Bradford assay. Cell lysates were mixed with methanol and hydrogen peroxide in assay buffer. Reaction was set for 20 minutes at room temperature. All samples were compared to assay buffer-treated cells (used as negative control). Catalase enzyme standard, derived from bovine liver, was used as positive control. Optical density changes at 540 nm were evaluated after addition of potassium hydroxide, Purpald and potassium periodate. For the assay, average absorbance was calculated and subtracted from the negative control for each sample and standards.

The results of this study are shown in Table 2. These results show the hydrogen peroxide degrading activity

TABLE 1

Hydrogen peroxide elimination activity of test agents

| | Yacon leave powder | | Amor Seco leave powder | | Dried Porphyridium biomass | |
|---|---|---|---|---|---|---|
| Agent (w/v) | Formaldehyde [µM] (Avg ± StDev) | Activity [nmol/min/mL] (Avg ± StDev) | Formaldehyde [µM] (Avg ± StDev) | Activity [nmol/min/mL] (Avg ± StDev) | Formaldehyde [µM] (Avg ± StDev) | Activity [nmol/min/mL] (Avg ± StDev) |
| 0.001% | 36.8 ± 22.6 | 1.8 ± 1.1 | 29.8 ± 13.9 | 1.5 ± 0.7 | 21.2 ± 1.0 | 1.1 ± 0.1 |
| 0.01% | 23.5 ± 5.6 | 1.2 ± 0.3 | 32.7 ± 9.6 | 1.6 ± 0.5 | 17.1 ± 2.0 | 0.9 ± 0.1 |
| 0.05% | 20.0 ± 4.6 | 1.0 ± 0.2 | 31.0 ± 11.2 | 1.5 ± 0.6 | 44.3 ± 12.8 | 2.2 ± 0.6 |
| 0.1% | 31.0 ± 16.5 | 1.5 ± 0.8 | 56.4 ± 21.3 | 2.8 ± 1.1 | 53.5 ± 18.1 | 2.7 ± 0.9 |
| 0.5% | 42.6 ± 16.5 | 2.1 ± 0.8 | 92.3 ± 8.7 | 4.6 ± 0.4 | * | * |
| 1% | 61.6 ± 23.9 | 3.1 ± 1.2 | 144.9 ± 18.7 | 7.2 ± 0.9 | * | * |
| 5% | 188.3 ± 22.0 | 9.4 ± 1.1 | 550.2 ± 20.8 | 27.5 ± 1.0 | * | * |

(*) The red-brown color of this natural extract, at higher testing concentrations, was stronger than the Purpald red-purple readout color, and therefore prevented an accurate reading of the results.

These results indicate that the dry leave powders of Amor Seco and Yacon and the dried *Porphyridium* biomass have high hydrogen peroxide eliminating activity, and therefore they are suitable, at concentrations of from about 0.001% (w/v) and higher, for use in the topical preparations of this disclosure.

Example 2

This study evaluated the effect of test materials on the endogenous cellular hydrogen peroxide degrading and eliminating activity of cultured normal human keratinocytes. Protein lysates of treated cells were used to measure hydrogen peroxide degrading activity using Purpald (4-amino-3- induced by each test agent within the treated keratinocytes, as compared to the endogenous activity of the untreated keratinocytes. All test materials produced a dose-responsive increase in the keratinocyte endogenous activity of hydrogen peroxide elimination. The untreated keratinocytes showed an activity of 1.5±0.2 Unit/mg protein (U/mg), and the test agents, at 0.5% (w/v), were able to increase this activity up to more than 210% (3.2±0.1 (U/mg)).

As a reference and for comparison, a *Camellia japonica* extract with a strong antioxidant activity, at 0.005%, was reported to enhanced catalase activity of HaCaT keratinocytes by about 50% only, and an ethanolic fraction of *Sargassum muticum* extract, at 10%, enriched for antioxidant activity, enhanced HaCaT cells catalase activity by 25% only [Antioxidant Effects of the Ethanol Extract from Flower of *Camellia japonica* via Scavenging of Reactive Oxygen Species and Induction of Antioxidant Enzymes. Mei Jing Piao, Eun Sook Yoo, Young Sang Koh, Hee Kyoung Kang, Junoh Kim, Yong Jin Kim, Hak Hee Kang and Jin Won Hyun, *Int. J. Mol. Sci.* 2011, 12:2618-2630), (Protective Effect of the Ethyl Acetate Fraction of *Sargassum muticum* Against Ultraviolet B-Irradiated Damage in Human Keratinocytes. Mei Jing Piao, Weon Jong Yoon, Hee Kyoung Kang, Eun Sook Yoo, Young Sang Koh, Dong Sam Kim, Nam Ho Lee and Jin Won Hyun, *Int. J. Mol. Sci.* 2011, 12:8146-8160).

TABLE 2 a: Catalase Assay measurements

| Test Group | Activity/total protein (U/mg) |
|---|---|
| Catalase enzyme (positive control) | 8.6 ± 0.6 |
| Untreated cells (negative control) | 1.5 ± 0.2 | b: Cellular hydrogen peroxide elimination, activity of test agents/total protein (U/mg)

| Test Material (%, w/v) | Yacon leave powder | Amor Seco leave powder | Dried Porphyridium biomass |
|---|---|---|---|
| 0.005 | 1.5 ± 0.1 | 2.0 ± 0.3 | 2.7 ± 0.1 |
| 0.05 | 1.8 ± 0.1 | 2.1 ± 0.4 | 3.0 ± 0.1 |
| 0.5 | 2.6 ± 0.1 | 2.5 ± 0.2 | 3.2 ± 0.1 |

The activity (U) is defined as nmol/min/mL. The activity is normalized to the total protein amount in each cell lysate sample, which is defined as U/mg.

These results show that exposure of human keratinocytes to Yacon leave powder, or Amor Seco leave powder, or dried *Porphyridium* biomass powder, results in an enhancement of the endogenous cellular activity of the keratinocytes, increasing their ability to remove, degrade or eliminate hydrogen peroxide. These results suggest that these agents could be used topically, for skin, scalp, hair and nail, to reduce hydrogen peroxide concentration, and therefore to be useful in this disclosure. The topical use of either Yacon leave powder, or Amor Seco leave powder or dried *Porphyridium* biomass powder, should slow, delay and reduce the progression of hair graying, which is initiated and enhanced by high endogenous hydrogen peroxide levels. Similarly, the topical use of Yacon leave powder, or Amor Seco leave powder, or dried *Porphyridium* biomass, should reduce the progression and the visibility of depigmented skin lesions, the signs of skin, scalp, hair, and nail aging, and the problems associated with geriatric skin.

Example 3

The purpose of this study was to evaluate intracellular antioxidant activity of test materials in cultured human epidermal keratinocytes, in response to a hydrogen peroxide insult. Cells were treated with test materials, labeled with H2DCFDA and later exposed to hydrogen peroxide. Relative fluorescence was measured as indicator for intracellular reactive oxygen species (ROS). The testing involved changes in fluorescence, which is proportional to an effective intracellular antioxidant activity when comparing untreated and hydrogen peroxide-only treated samples.

Test agents were stored at room temperature until use. Sample powders were suspended in phosphate buffer (1×PBS) to make 10 mg/mL (1% w/v) stock solutions, vortexed for 1 minute, sonicated on ice for 10 minutes at 30-50% output, centrifuged at 1000 rpm for 10 minutes at 4° C., and the supernatants were sterilized using 0.2 μm-syringe filter. Such homogenized solutions were prepared for each test material.

Primary normal human epidermal keratinocytes (NHEKs) were seeded on 96-well plates and cultured until reaching 75-80%. Subsequently, cells were treated with or without test materials in culture media for 24 hours. Test materials were created by diluting (1:10) the stock solutions in fresh EpiLife medium to make 0.05 and 0.1% (w/v) final concentrations. Untreated cells received equal volume of fresh EpiLife medium without test materials. At 24 hours, cells were labeled with the cell-permeant 2',7'-dichlorodihydrofluorescein diacetate (H2DCFDA) for 60 minutes and intracellular ROS levels were induced with hydrogen peroxide treatment (250 μM) for 30 minutes. Relative fluorescence at 492 nm (Excitation) and 535 nm (Emission) was measured using a plate reader.

Average fluorescence was calculated for each sample and compared to untreated (no $H_2O_2$) cells used as negative control. Results produced by $H_2O_2$-only treated cells showed that hydrogen peroxide produced a significant increase in relative fluorescence indicating an increase in intracellular ROS levels.

The results of this study are shown in Table 3. Amor Seco leave extract and Yacon leave extract produced a significant decrease in relative fluorescence when tested at 0.05% (w/v) and 0.1% (w/v). Amor Seco leave extract induced an intracellular anti-ROS activity with 92-100% inhibition. Yacon leave extract led to a 49-67% inhibition. The *Porphyridium* biomass extract could not be evaluated in this study, as its fluorescence analysis documented strong auto-fluorescence that masked the readout of this assay.

TABLE 3 a: Summary results of H2DCFDA fluorescence*

| Test Material | % Relative Fluorescence (Sample/Untreated) | |
|---|---|---|
| | Average | SEM |
| Untreated | 100.0 | 0.7 |
| H2O2 (0.25 mM) | 251.9 | 9.5 |
| H2O2 + Yacon (0.05%) | 133.2 | 13.0 |
| H2O2 + Yacon (0.1%) | 156.6 | 15.1 |
| H2O2 + Amor Seco (0.05%) | 111.5 | 5.2 |
| H2O2 + Amor Seco (0.1%) | 94.7 | 3.6 |

*Data shown represent mean ± SEM of relative fluorescence from two independent experiments (same experimental design run at different dates)

b: Summary results of ROS inhibition*

| Test Material | Average ROS Inhibition (%) | |
|---|---|---|
| | Average | SEM |
| Yacon (0.05%) | 66.8 | 10.4 |
| Yacon (0.10%) | 48.7 | 12.7 |
| Amor Seco (0.05%) | 92.3 | 3.0 |
| Amor Seco (0.10%) | 103.5 | 2.1 |

*Data shown represent mean ± SEM of ROS inhibition from two independent experiments (same experimental design run at different dates)

These results show that exposure of human keratinocytes to Yacon leave powder, or Amor Seco leave powder, results in an enhancement of the endogenous cellular ability to remove, degrade or eliminate hydrogen peroxide. These results suggest that these agents could be used topically, for skin, scalp, hair and nail, to reduce hydrogen peroxide concentration, and therefore to be useful in this disclosure. As previous results (Example 1 and Example 2) showed that the dried *Porphyridium* biomass increased catalase activity greater than Yacon or Amor Seco leave extracts, it is expected that the dried *Porphyridium* biomass would produce superior results in this assay too.

The topical use of either Yacon leave powder, or Amor Seco leave powder or dried *Porphyridium* biomass powder, should slow, delay and reduce the progression of hair graying, which is initiated and enhanced by high endogenous hydrogen peroxide levels. Similarly, the topical use of Yacon leave powder, or Amor Seco leave powder, or dried *Porphyridium* biomass, should reduce the progression and the visibility of depigmented skin lesions, the signs of skin, scalp, hair, and nail aging, and the problems associated with geriatric skin.

Combining the knowledge of these studies, it is expected that the topical treatment with the natural agents of this disclosure would deliver the hydrogen peroxide eliminating activity of the agents themselves, and would additionally enhance the endogenous hydrogen peroxide breakdown or elimination activity of the keratinocytes. The effectiveness of these agents is expected at concentrations of from about 0.001% (w/v of powdered natural) and higher.

Example 4

Preparation of natural extract gel formulations. Natural extracts can be prepared as liquid samples (suspensions) or as sample powders of the natural source that are suspended in water or phosphate buffer or other aqueous solutions, to make e.g. 10-100 mg/mL (1-10% w/v) stock suspensions. The suspensions should be mixed (e.g. vortexed) for e.g. 1-10 minute, and the natural material should then be size-reduced, e.g. at 4° C., to break down the cells (e.g. by pressure disruption, jet milling, ball milling, or sonication e.g. for 10 minutes at e.g. 30-50% output). Larger particles should then be separated (e.g. by centrifugation at 500-1000 rpm for 10 minutes at 4° C.), and the pellets should be discarded. The supernatants can be directly used in the formulation, or could undergo a further size selection (e.g. the suspension or solution can be filtered using a 0.2 micron pore size filter). The resulting homogenized solutions of the naturals could be directly used in the formulations, or could be further dried (e.g. lyophilized, spray dried or freeze-dried), and used in the formulation as dry powders.

Limited examples of some gel compositions suitable for this invention are suggested in Tables 4. A preservative (e.g. Phenonip®, phenoxyethanol), and/or a chelating agent (e.g. Disodium EDTA), and/or a humectant (e.g. glycerin) could be added first to the natural extract (which is in a liquid form or a powder suspended in liquid, e.g. water). At this step it is also possible to further add to the natural extract mixture oil-soluble silicones, emollients, viscosity builders or emulsifiers (e.g. cyclomethicone, dimethicone, PolySorbate 20, Aluminum Starch Octyl Succinate, Sucrose Cocoate, PEG-6 Capric/Caprylic Triglycerides). It is suggested to prepare a second mixture of a thickener(s) (e.g. Sepigel®, PolyAquol 2W) along with an anti-oxidant (e.g. BHT). The two mixtures should then be combined and mixed until homogeneity. Other anti-oxidants (e.g. ascorbic acid, sodium ascorbyl phosphate, lactoferrin, or tocopherol) could then added to the combined mix and evenly mixed to form the resulting gel.

TABLE 4

| CTFA name | % W/W | % W/W | % W/W | % W/W | % W/W | % W/W | % W/W | % W/W | Average standard ranges |
|---|---|---|---|---|---|---|---|---|---|
| Natural extract (liquid) | 87.3 | 89.29 | 96.33 | 96.3 | 95.9 | 96.4 | | | 0-100 |
| Natural extract (powder) | | | | | | | 1.0 | 5.0 | 0-25 |
| Deionized water | | | | | | | 94.8 | 90.9 | 0-100 |
| L-methionine | 0.1 | | 0.01 | | 0.05 | | 0.1 | | 0-1 |
| Phenoxyethanol | 0.75 | 0.75 | 0.75 | 0.75 | 0.75 | | 1.0 | 1.0 | 0-5 |
| Glycerine | 2.5 | 2.5 | | | | | | | 0-5 |
| Cyclomethicone | 2.0 | | | | | | | | 0-5 |
| Aluminum Starch Ocetyl Succinate | 0.75 | | | | | | | | 0-5 |
| Sucrose Cocoate | 1.0 | 1.0 | | | | | | | 0-5 |
| PEG-6 Capric/Caplylic Triglycerides | 3.0 | 3.0 | | | | | | | 0-5 |
| Disodium EDTA | 0.1 | 0.1 | | | 0.05 | | 0.05 | 0.05 | 0-1 |
| Polyacrylamine/Laureth-7/C$_{13-14}$ Isoparaffin | 2.5 | 2.75 | 2.9 | 2.9 | 3.2 | | 3.0 | | 0-5 |
| Ascorbic Acid | | 0.01 | | | | | | | 0-1 |
| Butylated Hydroxytoluene | 0.1 | 0.1 | 0.01 | 0.05 | 0.05 | 0.1 | 0.05 | 0.05 | 0-1 |
| Polysorbate 20 | | 0.5 | | | | | | | 0-2 |
| PolyAquol 2W | | | | | | 3.5 | | 3.0 | 0-6 |

Example 5

Preparation of natural extract oil-in-water formulations. The natural extracts can be prepared as in example 4. Two examples of oil-in-water emulsions are presented in Table 5. To prepare this type of formulation, the ingredients of the lipid phase should be combined and mixed at about 50-85°

C., and then cooled to about 40-60° C. In a separate vessel, the thickener can be slowly combined with the aqueous natural extract or the powder natural extract reconstituted in water or an aqueous solution. After mixing for e.g. about ten minutes the rest of the aqueous phase ingredients can be added and mixed, and then heated to about the lowest possible temperature of the lipid phase. The two phases can then be combined, mixed for e.g. for about ten minutes, and cooled to room temperature. Additional active agents may be combined into both phases or after their mixing. The biological activity described in this disclosure should be monitored, as excessive heat could reduce the desired activity.

TABLE 5

| Phase | CTFA Name | % W/W | % W/W | Average standard ranges |
|---|---|---|---|---|
| OIL | Cetearyl Glucoside | 1.4 | 1.4 | 0.1-2.8 |
| | C12-15 Alkyl Benzoate | 4.0 | 4.0 | 1-6 |
| | Octyl Hydroxystearate | 1.0 | 1.0 | 0-5 |
| | Dimethicone | 1.0 | 1.0 | 0-5 |
| | Cyclomethicone | 1.0 | 1.0 | 0-5 |
| | Cetyl Alcohol | 2.5 | 2.5 | 0-4 |
| | Butylated Hydroxytoluene | 0.1 | 0.1 | 0-0.5 |
| | Octyl Methoxycinnamate | 6.0 | 6.0 | 0-10 |
| | Vitamin E acetate | 0.5 | 0.5 | 0-0.5 |
| | Tocopherol Acetate | 0.5 | 0.5 | 0-0.5 |
| AQUEOUS | Glycerine | 3.0 | 3.0 | 0-20 |
| | D-Pathenol | 0.5 | 0.5 | 0-5 |
| | Disodium EDTA | 0.1 | 0.1 | 0.01-1 |
| | Phenoxyethanol | 0.7 | 0.3 | 0-1 |
| | L-methionine | 0.1 | 0.05 | 0-1 |
| | Carbomer | 0.35 | 0.3 | 0-3 |
| | Deionized Water | 76.25 | | 50-80 |
| | Natural extract in liquid form | | 77.5 | 0.001-90 |
| | Natural extract in powder form | 1.0 | | 0.001-20 |
| | Other cosmetic or therapeutic agents | 0 | 0.25 | 0-10 |

Example 6

Preparation of natural extract water-in-oil formulations. The natural extracts can be prepared as in example 4. Two examples of water-in-oil formulations are presented in Table 6. To prepare this type of formulation the emollients (e.g. mineral oil) can be melted. The other oil phase ingredients can then be added and the mixture can be heated e.g. to about 75° C. to enable homogeneous mixing. The aqueous phase ingredients can be mixed separately and should be warmed to the lowest possible temperature of the liquid oil phase (while confirming the retaining of biological activity of the natural extract), and then the two mixture can be stirred until it congealed. Additional active agents may be combined into both phases or after their mixing.

TABLE 6

| Phase | CTFA Name | % W/W | % W/W | Average standard ranges |
|---|---|---|---|---|
| OIL | Mineral Oil | 25.0 | 25.0 | 40-80 |
| | Sorbitan Monooleate | 5.0 | 5.0 | 1-6 |
| | Stearyl Alcohol | 25.0 | 25.0 | 20-60 |
| | Dimethicone | 1.0 | 1.0 | 1-5 |
| | Cetyl Alcohol | 2.0 | 2.0 | 0.1-10 |
| | Hydrogenated Lecithin | 3.0 | 3.0 | 0-10 |
| | Parsol MCX | 3.0 | 3.0 | 0-10 |
| | Vitamin E acetate | 0.5 | 0.5 | 0.01-0.5 |
| AQUEOUS | Glycerine | 3.0 | 3.0 | 0-20 |
| | Phenoxyethanol | 0.7 | 0.7 | 0.01-1 |
| | Deionized Water | 30.79 | | 20-45 |
| | Natural extract in liquid form | | 31.55 | 20-45 |
| | Natural extract in powder form | 1.0 | 0 | 0-10 |
| | L-methionine | 0.01 | | 0-1 |
| | Other active agents | 0 | 0.25 | 0-1 |

It is understood that while the disclosure has been described in conjunction with the detailed description thereof, that the foregoing description is intended to illustrate and not limit the scope of the disclosure.

What is claimed is:

1. A method for improving the condition of geriatric skin, comprising applying to the skin of a subject over about age 65, a non-denatured composition comprising a soluble aqueous extract of *Porphyridium* biomass and a pharmaceutically or cosmetically acceptable carrier, wherein the aqueous extract is non-denatured and the non-denatured extract has a hydrogen peroxide degrading activity of (i) at least 2 nmol/min/ml at 0.5% (w/v) or (ii) an activity of enhancing, by at least 50% the endogenous keratinocyte hydrogen peroxide degrading and eliminating activity, at 0.5% (w/v), wherein the soluble aqueous extract is free of insoluble *Porphyridium* material.

2. The method of claim 1 wherein the composition further comprises L-methionine.

3. The method of claim 1 wherein the source of the *Porphyridium* biomass was grown under conditions that enrich for L-methionine.

4. The method of claim 1 wherein the composition comprises one or more of: a stabilizer, emulsifier, thickener, permeation enhancer, preservative, surfactant, chelating agent, humectant and anti-oxidant.

5. The method of claim 1 wherein the method (i) slows the thinning of skin, or (ii) reduces the dryness of skin, or (iii) reduces skin pruritis, or (iv) reduces the severity of hematoma development, or (v) enhances the healing of superficial wounds of the skin, and/or (vi) reduces skin fragility.

6. The method of claim 1, wherein applying the composition reduces hydrogen peroxidase concentration in the geriatric skin.

7. The method of claim 1, wherein the soluble aqueous extract is a soluble aqueous extract of lysed *Porphyridium* biomass.

* * * * *